US012622653B2

(12) United States Patent
Ritter et al.

(10) Patent No.: US 12,622,653 B2
(45) Date of Patent: May 12, 2026

(54) METHOD AND APPARATUS FOR RECONSTRUCTING CT IMAGES

(71) Applicant: Siemens Healthineers AG, Forchheim (DE)

(72) Inventors: Andre Ritter, Neunkirchen am Brand (DE); Thomas Allmendinger, Forchheim (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 316 days.

(21) Appl. No.: 18/161,289

(22) Filed: Jan. 30, 2023

(65) Prior Publication Data

US 2023/0306659 A1 Sep. 28, 2023

(30) Foreign Application Priority Data

Jan. 31, 2022 (DE) ..................... 10 2022 200 999.1

(51) Int. Cl.
*A61B 6/03* (2006.01)
*A61B 6/00* (2024.01)
*G06T 11/00* (2006.01)

(52) U.S. Cl.
CPC ............ *A61B 6/032* (2013.01); *A61B 6/5205* (2013.01); *A61B 6/54* (2013.01); *G06T 11/006* (2013.01); *G06T 11/008* (2013.01); *G06T 2210/41* (2013.01)

(58) Field of Classification Search
CPC . G06T 11/008; G06T 11/006; G06T 2210/41; G06T 2211/424; G06T 2211/441; G06T 11/005; A61B 6/032; A61B 6/5205; A61B 6/54; A61B 6/5241; G06N 3/0464
See application file for complete search history.

(56) References Cited

U.S. PATENT DOCUMENTS

| | | | | |
|---|---|---|---|---|
| 9,262,831 B2 * | 2/2016 | Münzenmayer | .......... | G06T 7/33 |
| 9,978,159 B2 * | 5/2018 | Kraus | ................... | G06T 11/006 |
| 10,854,329 B2 * | 12/2020 | Mohr | ..................... | A61B 6/507 |
| 11,176,428 B2 * | 11/2021 | Lee | ......................... | G01T 1/161 |

(Continued)

FOREIGN PATENT DOCUMENTS

| | | |
|---|---|---|
| CN | 101512602 A | 8/2009 |
| CN | 103027705 A | 4/2013 |

(Continued)

OTHER PUBLICATIONS

Lebedev, Sergej et al: "Stack transition artifact removal for cardiac CT using patch-based similarities". In: Medical Imaging 2018: Physics of Medical Imaging. SPIE, 2018. pp: 487-492.

(Continued)

*Primary Examiner* — Juan M Guillermety
(74) *Attorney, Agent, or Firm* — Harness, Dickey & Pierce, P.L.C.

(57) ABSTRACT

A method for reconstructing CT images, comprises: providing CT recording data; reconstructing overlapping partial images; establishing displacement vectors for registering overlap regions of the partial images; interpolating a displacement vector field for each partial image from associated sets of the displacement vectors of the two side regions; creating an output image dataset based on the CT recording data and the displacement vector fields; and outputting the output image dataset.

28 Claims, 4 Drawing Sheets

(56)            References Cited

U.S. PATENT DOCUMENTS

| | | | |
|---|---|---|---|
| 2007/0232888 A1* | 10/2007 | Bruder .................. | A61B 6/503 |
| | | | 600/407 |
| 2010/0014736 A1 | 1/2010 | Barschdorf et al. | |
| 2011/0235884 A1 | 9/2011 | Schreibmann et al. | |
| 2012/0093278 A1* | 4/2012 | Tsukagoshi ........... | G06T 11/008 |
| | | | 345/682 |
| 2014/0044329 A1 | 2/2014 | Veerman et al. | |
| 2017/0091930 A1* | 3/2017 | Kozuka .................. | G06T 19/00 |
| 2018/0040145 A1* | 2/2018 | Matthews ............. | G06T 11/005 |
| 2018/0150962 A1* | 5/2018 | Fletcher .................... | G06T 7/35 |
| 2021/0295574 A1 | 9/2021 | Grass et al. | |
| 2021/0296089 A1 | 9/2021 | Zeidler et al. | |

FOREIGN PATENT DOCUMENTS

| | | | |
|---|---|---|---|
| CN | 103493098 A | 1/2014 | |
| CN | 104299209 A | 1/2015 | |
| CN | 109716394 A | 5/2019 | |
| CN | 111179373 A | 5/2020 | |
| CN | 111260705 A | 6/2020 | |
| DE | 102010005266 A1 | 7/2011 | |
| DE | 102011083646 A1 | 3/2013 | |
| DE | 102012206733 A1 | 10/2013 | |
| JP | 2013215472 A | 10/2013 | |

OTHER PUBLICATIONS

Lebedev S. et al.:., "Stack Transition Artifact Removal (STAR) for Cardiac CT", 2019, Magphan S162&128, www.phantomlab.com.
Wang Tingting et al:; "Patch-Based Super-Resolution Reconstruction for Lung 4D-CT Images"; Apr. 20, 2015.
Zhang Jie et al:; "Slice Interpolation for MRI Using Surface Fitting with Registration Method"; Apr. 30, 2016.

\* cited by examiner

METHOD AND APPARATUS FOR RECONSTRUCTING CT IMAGES

CROSS-REFERENCE TO RELATED APPLICATION(S)

The present application claims priority under 35 U.S.C. § 119 to German Patent Application No. 10 2022 200 999.1, filed Jan. 31, 2022, the entire contents of which are incorporated herein by reference.

FIELD

One or more example embodiments of the present invention relate to a method and an apparatus for reconstructing CT images, in particular for a CT stack artifact correction method.

BACKGROUND

In CT (computed tomography) imagingin the region of the thorax, movements such as, for example, the heartbeat or changes in the lungs caused by breathing can lead to inconsistent recording data. CT images which are reconstructed from inconsistent recording data show these inconsistencies in the CT images as artifacts in the form of "blurred" structures or discontinuities such as jumps at transitions.

These artifacts can be reduced in that, for example, by way of high rotation speeds or dual source techniques, the time span that is needed to cover a suitable rotation angle interval during a recording is lessened. If the typical length scales on which a change takes place within this time interval are small compared with the voxel spacings (ca. 1 mm) achieved later, then the artifacts are also small, but still present.

For the reduction of these artifacts, in a known movement pattern, the recording is often performed with defined movement conditions. In order to achieve this, in, for example, cardiac imaging with CT, apart from the temporal resolution, above all the control of the recording and reconstruction via the analysis of an ECG signal obtained during the recording plays an important part. Normally, above all, the data which can be obtained or taken into account in the reconstruction during a defined rest position of the heart are recorded.

In recordings of an extended region, there is a particular difficulty. The recording region of a CT detector often does not necessarily cover a desired recording region along the CT axis (e.g. that of the heart) completely. A complete coverage is then achieved, for example, by way of a continuous table feed during the recording (spiral CT) or by way of a table feed between a plurality of successive recordings with a static patient (sequence CT). The consequence thereof is that data from the same recording time point is not present for all the positions along the CT axis used in the recording. In particular, during the recording of the heart, it is thus possible that for two different positions, only data from different heart cycles is available. Or conversely, for the same position, data from a plurality of heart cycles is available. It can occur that recording data which originates from comparable regions of a plurality of heart cycles nevertheless has spatial differences, for example, by way of an overlaid breathing movement or other differences between the heart cycles which cannot necessarily be represented and recognized in the ECG. Thereby, despite a high temporal resolution, inconsistent data can arise, which can find expression therein that in the reconstructed CT image, overlaid structures from a plurality of heart cycles are recognizable. However, for example, discontinuities between the slices can also arise, since for instance, subregions are so greatly displaced during the patient movement that they cannot be captured by the detector region in any of the heart cycles.

In special SOMATOM CT scanners, the possibility of a so-called True Stack reconstruction exists. Herein, each CT layer is reconstructed from only a single defined heart cycle, even if there were recording data from a plurality of heart cycles for one slice. Therein, coherent slice stacks (stacks) which can be associated with exactly one determined heart cycle (thus also a time point) are formed. A plurality of such stacks can then follow one another. In each stack, it can be assumed that artifacts evoked by movement only play a part if the time interval for the recording of this stack is too large, as described above.

If there are inconsistencies between the stacks (e.g. due to breathing movement), then this can reveal itself in that discontinuities arise at the boundary between two stacks. These are distinguished by truncated structures or doubled structures along the CT axis.

A further-developed method for solving the discontinuity problem at stack boundaries has been disclosed by Lebdev et al. in "Stack Transition Artifact Removal (STAR) for Cardiac CT" (Med. Phys. 46 (11), 4777-4791; November 2019). This is based on forming a displacement vector field via image registration, on the basis of which the discontinuities at the stack boundaries are lessened in that the image structures are deformed according to the vector fields thus obtained. For this purpose, the fact is made use of that the stacks usually have a greater coverage than the finally displayed coverage along the CT axis. By this mechanmism and/or means, an overlap region of the stacks is formed in which the image data of both stacks is present and in which an image registration can then be carried out.

SUMMARY

It is an object of one or more example embodiments of the present invention to provide an alternative, convenient method and a corresponding apparatus for reconstructing CT images, with which the aforementioned disadvantages can be avoided.

At least this object is achieved by a method according to one or more example embodiments of the present invention, an apparatus according to one or more example embodiments of the present invention, as well as by a control device according to one or more example embodiments of the present invention and/or a computed tomography system according to one or more example embodiments of the present invention.

One or more example embodiments of the present invention serve for reconstructing CT images, in particular for a CT stack artifact correction method. If the reconstruction is carried out by a CT system or a diagnostic unit, one or more example embodiments of the present invention serve also for controlling the CT system or the diagnostic unit under consideration. In particular, by way of one or more example embodiments of the present invention, image data is altered such that images assembled from a plurality of stacks can be created without discontinuities.

The method according to one or more example embodiments of the present invention comprises the following steps:

providing CT recording data comprising recordings of a plurality of overlapping partial image volumes, reconstructing a working image dataset from the CT recording data, wherein the working image dataset comprises a plurality of partial images, wherein each partial image has an overlap region with at least one other partial image, establishing displacement vectors for registering the overlap regions of the partial images to one another, wherein a set of displacement vectors is associated with each partial image of the working image dataset for two opposing side regions in each case, wherein in the event that a side region is not registered to another side region, a set of predetermined displacement vectors is associated with this side region, interpolating a displacement vector field for each partial image from its sets of the displacement vectors of the two side regions, wherein two sides of the displacement vector field correspond to the respective sets of established displacement vectors for this partial image and the displacement vectors are interpolated between the two sides on the basis of a predetermined transfer function from one set of displacement vectors to the other set of displacement vectors, creating an output image dataset on the basis of the CT recording data and the displacement vector fields, outputting the output image dataset.

The provided CT recording data do not comprise reconstructed data. This can be, for example, raw data or preprocessed data. The provision can take place by way of recording the data via a CT scanner or by accessing already recorded data in a storage device, e.g. via a PACS (Picture Archiving and Communication System).

The CT recording data comprises or consists of a plurality of recordings of overlapping partial image volumes which represent a motif in total. In particular, these are recordings of the heart region, for example ECG-controlled CT recording of the lungs or the heart. To each recording can therein be assigned, in particular, an individual movement state of the respective partial volume, in particular a defined heart cycle.

The structure of the CT recording data can be imagined such that it comprises raw partial images which, grouped together, would provide the entire motif. However, since CT data must be reconstructed laboriously in order to produce an image, these raw partial images can appear as datasets of raw data or preprocessed raw data which would produce partial images when reconstructed.

The specific strengths of one or more example embodiments of the present invention lie in the reconstruction of images that have movement artifacts. The recording is to be made "movement triggered", i.e. at pre-defined time points, recordings of partial volumes have been made, e.g. during a particular state in the heart cycle or during breathing. In particular, a movement should be known, for example, because it is cyclical or its sequence is well known. In principle, however, one or more example embodiments of the present invention can also be used for other CT recording data, for example, in order to compensate for movement artifacts from disturbances to the CT scanner. In particular, the CT recording data contains data relating to images which can be associated with a single fixed heart cycle of the patient. The recording of the heart of the patient therein takes place over a plurality of cycles, typically over 2 to 4 cycles (in a triggered sequence) or 5 to 8 cycles (in a gated spiral). In both techniques, the recording provides for an overlap of the data of the partial images. This overlap is typically approximately 10% of the length of the partial volume (in the spiral up to 20%) so that an overlap region can readily be found.

From the CT recording data, partial images (also referred to as "stacks") are reconstructed. These partial images represent the recorded partial image volumes (parts of the overall motif) and together form a working image dataset. They (or the working image dataset) are still not intended for diagnosis, but serve only for carrying out the method. They also do not have to have the best resolution, but can certainly have a lower resolution than the output image dataset created later. The working image dataset preferably has properties needed by the registration method, which cannot be influenced by the CT user.

As far as these properties are concerned, a specified image resolution is to be mentioned, for example, realized by the predetermined selection of a reconstruction convolution kernel and a specified slice thickness and slice spacings suitable therefor and x-y grid spacings of the voxels in the slices. Requirements are also often placed on the minimum size of the image portion, so that a sufficiently large image region is available for registration, even if the user selects a very small image portion. It is advantageous for a standardized preparation of recordings to be evaluated if a user is unable to change (all) these properties, in order not to falsify important preconditions for a diagnosis accidentally.

Each partial image of the working image dataset must overlap with at least one other partial image. Therein, the individual partial images which overlap only with a single partial image should lie at the edge and partial images not at the edge (e.g. in the middle) should overlap with at least two partial images. It is generally advantageous if all the boundaries of partial images which represent the desired part of the motif represent an overlap region between at least two partial images. "Overlap region" and "overlap" are taken to mean that a partial volume of the recording region (the motif) is represented there in each of the relevant partial images. The overlap region should preferably amount to at least 1% of a partial image, in particular at least 5%. The overlap region is typically at the edge of a partial image.

If these partial images are present, they are assembled by way of the method. It is here that the first difficulties arise, that the partial images typically do not fit together exactly at their overlap regions, since the motif has changed between the recording of the partial images, e.g. a heart, due to the heartbeat. In order to overcome these difficulties, displacement vectors for registering the overlap regions of the partial images to one another are established. In a rough approximation, it can be stated that the displacement vectors indicate which image points (or rather: which image values) must be displaced to where, so that the partial images fit together at their overlap region.

In the course of this, a set of displacement vectors is associated with each partial image of the working image dataset in each case for two opposite side regions. However, it must be noted herein which partial images lie at the edge and which do not lie at the edge. If the side region is an overlap region, then displacement vectors can be easily calculated. If the side region is an edge (not an overlap region), then a set of predetermined displacement vectors is associated therewith, e.g. zero vectors.

Up to this point, the partial images now fit together, but in the overlap region, they can possibly be distorted by way of the displacement vectors such that the problem of artifacts is displaced only from the image edge further into the middle of the partial image. This problem is solved by the subsequent step which achieves an adaptation of the entire partial image.

In order to "harmonize" the partial image, a displacement vector field is interpolated from the displacement vectors. The expression "interpolated" is taken to mean that a continuous transition from displacement vectors in the one side region to displacement vectors in the other side region is created. Therein, two sides of the displacement vector field (where the side regions of the partial images are) correspond to the respective sets of established displacement vectors for this partial image. Therebetween, the displacement vectors are interpolated on the basis of a transfer function from one set of displacement vectors to the other set of displacement vectors, so that a transition from one side to the other side takes place. For example, all three spatial coordinates of a displacement vector can be calculated between the sides via a weighted function from the coordinates of two displacement vectors at the sides, wherein the weighting takes account of the spacing of the calculated displacement vector from the two other displacement vectors at the sides.

In order to ensure a harmonious image impression, it is preferred that adjoining vectors (both in the overlap region and also at other sites in the partial image) have a predetermined similarity, that is, no over-adaptation exists, but rather a "smoothness" of the displacement vector field is ensured.

Via the displacement vector field, a partial image can be rectified during an adaptation to adjacent partial images and, from the CT recording data, an output image dataset can be generated. The output image dataset can now have the desired resolution for diagnosing. The reconstruction can take place so that the partial images are distorted via the displacement vector fields and then assembled or that with the information items of the displacement vector fields, once again a new reconstruction of the CT recording data is started.

The output image dataset is then output, for example, to a storage device (e.g. a PACS) and/or to a display unit and can be viewed there by a diagnosing person.

The apparatus according to one or more example embodiments of the present invention comprises the following components:

a data interface designed to receive CT recording data comprising recordings of a plurality of overlapping partial image volumes, a working reconstruction unit designed for reconstructing a working image dataset from the CT recording data, wherein the working image dataset comprises a plurality of partial images, wherein each partial image has an overlap region with at least one other partial image, a displacement unit designed for establishing displacement vectors for registering the overlap regions of the partial images to one another, wherein a set of displacement vectors is associated with each partial image of the working image dataset for two opposing side regions in each case, wherein in the event that a side region is not registered to another side region, a set of predetermined displacement vectors is associated with this side region, a vector field unit designed for interpolating a displacement vector field for each partial image from its sets of the displacement vectors of the two side regions, wherein two sides of the displacement vector field correspond to the respective sets of established displacement vectors for this partial image and the displacement vectors are interpolated between the two sides on the basis of a predetermined transfer function from one set of displacement vectors to the other set of displacement vectors, a second reconstruction unit designed for creating an output image dataset on the basis of the CT recording data and the displacement vector fields, a data interface for outputting the output image dataset.

A control device according to one or more example embodiments of the present invention for controlling a computed tomography system is designed for carrying out a method according to one or more example embodiments of the present invention and/or comprises an apparatus according to one or more example embodiments of the present invention.

A computed tomography system according to one or more example embodiments of the present invention comprises a control device according to one or more example embodiments of the present invention.

A majority of the aforementioned components of the apparatus can be realized entirely or partially in the form of software modules in a processor of a corresponding computer system, for example, by a control device of a computed tomography system. A realization largely through software has the advantage that conventionally used computer systems can also easily be upgraded with a software update in order to operate in the manner according to one or more example embodiments of the present invention. In this respect, the object is also achieved via a corresponding computer program product with a computer program which is loadable directly into a computer system, having program portions in order to carry out the steps of the method according to one or more example embodiments of the present invention, at least the steps that can be executed by a computer when the program is executed in the computer system. Such a computer program product can comprise, apart from the computer program, additional components, if relevant, such as for example, documentation and/or additional components including hardware components, for example, hardware keys (dongles, etc.) in order to use the software.

For transport to the computer system or to the control device and/or for storage at or in the computer system or the control device, a computer-readable medium, for example, a memory stick, a hard disk or another transportable or firmly installed data carrier can be used on which the program portions of the computer program which can be read in and executed by a computer system are stored. For this purpose, the computer system can have, for example, one or more cooperating microprocessors or suchlike.

Further particularly advantageous embodiments and developments of the present invention are disclosed by the dependent claims and the following description, wherein the claims of one claim category can also be further developed similarly to the claims and description passages relating to another claim category and, in particular also, individual features of different exemplary embodiments or variants can be combined to new exemplary embodiments or variants.

According to a preferred method, for establishing displacement vectors for registering an overlap region between a first partial image and a second partial image, a two-dimensional boundary slice in the overlap region is determined. Preferably, the boundary slice is a plane and, particularly preferably, arranged perpendicularly to the CT axis, in particular in a central position within the boundaries of an overlap region.

Here and in the description below, the axis along which the table advance takes place or the axis along which the patient is moved relative to the CT scanner is regarded as the CT axis. If a plurality of partial images, which are to be assembled are recorded, the CT axis is thus the axis which extends from above downwardly by way of the partial images, that is, essentially orthogonally through the overlap regions.

Preferably, for determining the boundary slice, initially a set of displacement vectors is assumed with a predetermined value (e.g. zero) and the position of the boundary slice along the CT axis is determined so that the quadratic differences of the image values (HU values of the image points in the respective images) are as low as possible from the outset. It is advantageous if a start is made with a displacement vector of length zero and the difference of the two images is checked from the respective stacks which, in principle, should be "identical" and congruent. If this is not the case (e.g. due to a real displacement of the two images), the two images are displaced until the difference is zero or is at least a minimum. Therein, displacement vectors are generated, in particular by way of a gradient descent method in which a cost function ("the difference of the two images") is minimized as the goal.

It should be noted that given a good selection of the position of the boundary slice, the method provides particularly good results. Thereafter it is preferable to optimize the individual displacement vectors, in particular in that the remaining quadratic differences are minimized. This should take place, in particular, making provision for a regularization term in the cost function.

According to a preferred method, in an overlap region of a partial image, a regular 2D grid of sampling points is defined and a displacement vector is associated with each sampling point which, starting from this sampling point, points to a location in this partial image the image value of which is to be associated with the origin location of the displacement vector.

For example, a plane is defined (boundary slice), which is to match in both partial images, e.g. exactly the center of the overlap region of partial images S1 and S2. Thereafter, the displacement vector V defines with the origin R (on the boundary slice) that the value of the voxel R+V is to be associated with the value R in the boundary slice. Thus, the location to which a displacement vector points in this example is the source of the value which is entered as a comparison into the boundary slice and thus contributed to minimizing the aforementioned difference.

Even if mathematically vectors relate to displacements of a point to another, it is common practice in this technical domain of the registration that vectors point away from the relevant points r in order to represent the desired deformations. Thus, an altered image region I' (after the deformation of the image region I) is determined with $I'(r)=I(r+v)$. In general, it can be stated that a deformation model $r'=D(r)$ exists which for each point in the space, supplies an associated point so that the deformed image $I'(r)=I(D(r))$. In the special case considered here, $D(r)=r+v(r)$, that is, starting from the point r (e.g. a sampling point), a displacement with the vector v to a point r+v. The resulting image impression therein suggests that the image points are displaced from r+v to r. The background is that in practice, at least the points r for which it is desired to determine the image values after the deformation are predetermined. They therein preferably lie on a regular grid. In another approach (starting from the originally regularly arranged grid points and "displacing" them), it can occur that an irregularly arranged grid of image points is obtained after the deformation. This results in the apparent advantage that no interpolation is needed, although it is then necessary to transfer the deformed grid back into a regular grid or to carry out an interpolation in this irregular grid. This interpolation is significantly more complex than if the interpolation is performed directly in the still regularly arranged grid and directly thereafter a regularly arranged grid is again obtained.

Preferably, a side region of this partial image is defined by way of the sampling points and a set of displacement vectors is associated with this side region, said set comprising the displacement vectors that are associated with these sampling points.

Preferably, the sampling points are arranged equidistantly and/or form an aforementioned boundary slice. Preferably, for each of the two partial images which define the boundary slice, there is a vector per sampling point, said vectors indicating the locations in the respective stacks, wherein the displacement vectors are obtained via an image registration method. From each displacement vector there results a displaced image point wherein the displacement vectors can begin at the midpoint of an image point or at a corner of the image point. Each displacement vector should point to an image point in exactly one stack and each displaced image point should lie on a corresponding mapping of the same image point in another partial image.

According to a preferred method, in the overlap region between a first partial image and a second partial image, displacement vectors are selected so that in the overlap region, a first displacement vector is associated with a sampling point of the first partial image and a second displacement vector is associated with a corresponding sampling point of the second partial image. The expression "corresponding" here signifies that the sampling points each show the same image regions of the motif. Preferably, the second displacement vector therein represents an inverse vector of the first displacement vector. An inverse vector is therein a vector with quantitatively the same components, but reversed sign.

Preferably, in order to determine the two displacement vectors, a predetermined measure is used for a similarity of image regions of the two partial images, in particular on the basis of a square of differences of image values. In place of the squared difference, however, another measure can be used for evaluating the similarity, for example, local cross-correlation (LCC) or mutual information (MI).

Particularly preferably, via an iterative method, a minimizing vector can be determined stepwise on the basis of the current image values and image value gradients of the two partial images and a predetermined step length at respectively displaced sampling points, and can be added to the displacement vector, wherein the minimizing vector is based upon the aforementioned measure. Therefore, in each step n, there exists an initial displacement vector vn and the next displacement vector vn+1 following this step is given by vn+1=vn+un wherein un is the minimizing vector determined in the step n.

It occurs in practice that below a predetermined (in practice, very low) limit value for the image values (e.g. with the unit HU), proportionally very severe low-frequency variations of the image value are recognizable in the image. These are to be regarded as unwanted artifacts. These artifacts are seen, for example, in the region of the air outside the patient and in the region of highly ventilated lung areas. These low-frequency variations lead to gradients in the image which strongly influence the determination of the aforementioned minimizing vectors. These image regions are preferably not ignored here (or are not processed), rather in place of the actual image value, it is merely a "saturated image value" that is assumed. The saturation can therein occur very hard in the sense of a stepped function (i.e. all the image values below the limit value are simply set to the value of the limit value and all those above it are retained) or a function can be used which makes the transition to the limit value constantly differentiable, e.g. with an error function, a sigmoid function or a trigonometric function. The aim therein is to set differences and thus gradients from the variations of the image value below the threshold to zero as far as possible, so that as far as possible they no longer play a part in the determination of the minimizing vector.

According to a preferred method, displacement vectors are therefore set for image regions of a partial image, the image value of which lies below a predetermined limit value, to a predetermined value (e.g. as described above, to the limit value or adapted according to a function). The designation "the image value of which" means the value of the image region (e.g. the voxel) which is displaced by the displacement vector. This has the advantage that for irrelevant regions which contribute little to the result, only a little computation time is needed.

The limit value preferably lies above the air CT value, in particular above −1000 HU and preferably below −800 HU. A use of this procedure in the determination of the aforementioned minimizing vectors is particularly preferred. This has the advantage, in particular, that low-frequency image value variations can no longer lead to a severe distortion.

According to a preferred method, in the interpolation of displacement vectors of the displacement vector field from one image region (e.g. a voxel) between the side regions the spacing of the relevant image region from the side regions is determined an, in particular weighted, relationship of the spacings from the side regions is determined, wherein the closer side region preferably receives the greater weight, a displacement vector is calculated from the vector addition of a first displacement vector in a side region and a second displacement vector in the other side region of the partial image and the ratio.

It is preferred that the displacement vectors found in the overlap region (e.g. at the boundary slice) are continued in the direction toward the center of the relevant partial image (that is, to the other side region) with a damping specified externally. In the course of this damping, the length of the displacement vectors is reduced to a minimum value (e.g. zero). This provides for a continuous transition between the overlap region (e.g. the boundary slice) and the remaining partial image. The length of this damped transition can be empirically determined or firmly specified by a user. This length is preferably between 5 mm and 10 mm.

According to a preferred method, a smoothing of displacement vectors in the overlap region and/or in the displacement vector field between the side regions is carried out. In the course of this smoothing, it is preferred that in an (in particular in each) aforementioned iteration step, for determining displacement vectors in the overlap region, in particular a boundary slice, a smoothing convolution or a low pass filtration is carried out, in particular a convolution with a Gaussian window. Alternatively or additionally, it is preferred that before an interpolation of displacement vectors of the two side regions for the displacement vector field, a convolution is carried out with a Gaussian window in the overlap region, in particular in its boundary slice.

There are different types of interpolation of displacement vectors which have different properties with regard to their frequency response. Preferably, a displacement vector is interpolated at an arbitrary site in the space between the two boundary slices in that the two boundary slices are initially (optionally) smoothed by convolution and the width of the smoothing can be, for example, proportional to the spacing between the boundary slice and the site to be interpolated. The location of the site is then initially projected perpendicularly onto the two boundary slices. Bilinear interpolation is then performed at the projected locations. And two image values are obtained. The two image values are then summed in a weighted manner. Under the boundary condition that the weights produce the sum 1. If the weights depend linearly upon the spacing between the boundary slices, the equivalent to a linear interpolation results between the boundary slices. Overall, this can be regarded as a trilinear interpolation. In particular, if the sampling points are situated on the (2D) boundary slices at the same x-y sites, this procedure can also be regarded as a trilinear interpolation in a 3D grid, wherein the grid comprises only two grid sites in the z-direction in each case.

According to a preferred method, in the context of the creation of the output image dataset, initially partial images are reconstructed and then image regions of the partial images are displaced according to the displacement vector fields associated with them and the partial images are then assembled.

According to an alternative preferred method, the displacement vector fields are taken into account in the reconstruction process, in particular in the context of a back projection, wherein in the event that a region of the output image dataset can be formed from information from more than one partial image, a weighting of the corresponding contributions of the relevant partial images is carried out.

It is preferred that the output image dataset has a greater image resolution than the working image dataset. This enables a faster execution of the method.

According to a preferred method, the output image dataset and/or partial images are reconstructed via a different weighting of temporal components of the CT recording data. In this context, weighting values are preferably determined for a plurality of image points (e.g. voxels) of the output image dataset or the partial images, wherein exactly one weight is assigned to a number of displacement vectors. For this purpose, it is particularly preferred to use a 3D image point grid and a weighting value is assigned to each grid point or a group of grid points. In this way, portions of the CT recording data that are more accurate than other parts can enter a reconstruction with a higher weighting.

A preferred method is used in the event that in an overlap region of a first partial image with a second partial image, image points are present in which a reconstruction is not possible, or only to a limited extent, due to lacking data. If corresponding data is present in the second partial image, then this lacking data is preferably enhanced on the basis of data and the displacement vector field of the second partial image for reconstruction of the image points of the first partial image. Alternatively, in the reconstruction of the output image dataset, the relevant image points of the second partial image are preferably used (and not the disadvantageous data of the first partial image).

In a 3D geometry with fan beam detector geometry, in an ECG-triggered recording, typically less data is available in the reconstruction than a coverage over 360° would require. This has the result that the image voxels which see a complete set of 180° readings in a parallel geometry and thus provide a complete image contribution, do not fill a simple cuboid geometry, but rather only do this in the inner kernel and then in a complex geometry, are only partially filled. This would involve the principle that voxels of a partial image or the output image dataset are reconstructed from information of other partial images.

A preferred specific method for the practice comprises the following steps:

1. ECG-controlled CT recording of the heart (either as a spiral CT or a sequential CT recording).
2. Reconstructing a registration image dataset from the CT recording data from which coherent partial image volumes of all the stacks (which is how the partial images are designated below, since they are so named in practice) contained in the recording can be extracted, wherein an individual defined heart cycle can be associated with each stack, wherein the registration image dataset (the large number of stacks or the working image dataset) can have properties which are needed, in particular, by the registration method and which cannot be influenced by the CT user.
3. Determining the overlap region of successive stacks and determination of a (two-dimensional) boundary slice in each overlap region.
4. Determining displacement vectors starting from equidistantly arranged sampling points within the boundary slice, wherein for each of the two stacks which define the boundary slice, one vector per sampling point shows the locations in the respective stacks wherein the displacement vectors are obtained via an image registration method.
5. Generating displacement vectors and associated heart cycle for arbitrary image points in the space on and between the boundary slices (that is of the displacement vector field), wherein all the image points always originate in an identical slice along the CT axis from the same heart cycle.
6. Generating a final image dataset taking account of the image center points displaced according to the displacement vectors, wherein the final image dataset has, in particular, properties which are specified by the CT user.

Regarding Step 2:

In the product implementation, two CT image volumes with the respective identical image point grid are reconstructed. Each slice of this grid along the CT axis is thus reconstructed doubled. If recording data from two heart cycles is available for a slice, the recording data of the first heart cycle enters the slice of the first volume and the recording data of the second heart cycle enters the slice of the second volume. Thus, image data is independently available for both cycles for this slice. In addition, for later extraction of the stack, for each slice, the information from which cycle it originates is reserved. From these two image volumes, by corresponding recombination of slices from both the image volumes, the stacks (or parts thereof) can be recovered.

Also preferred is the embodiment in which for each heart cycle, a complete image volume is reconstructed in a targeted manner. The image data of a stack is then directly available by way of the reconstruction separately in individual image volumes.

In the reconstruction of the registration image dataset, the reconstruction is carried out in a manner such that the image data is particularly suitable for the purpose of the registration. For this purpose, in particular, a predetermined image resolution and a suitable image portion are relevant. The predetermined image resolution is achieved in that a predetermined reconstruction kernel is specified with image point spacings in the slice that are advantageous therefor. In addition, the slice thickness and the slice spacing are specified. The selection of the spacings takes place taking account of the sampling theorem so that an aliasing-free sampling of the image signal is provided. The image portion is selected so that it contains a "safety frame" round the image portion later desired by the CT user. By this mechanism and/or means, inaccuracies which arise by way of later convolution operations at the image boundaries during the image registration in the edge region can be kept away from the user image portion.

Regarding Step 3:

From the known boundaries of the stack, the regions of the overlap can be determined. In the product implementation, a boundary slice perpendicular to the CT axis, in a central position within the boundaries of an overlap region is selected.

Regarding Step 4:

For each boundary slice, the image registration between the two stacks which define the boundary slice is carried out.

In the boundary slice, a regular 2D grid of sampling points is assumed. A displacement vector which points, starting from the center point of the sampling point at a location in the first stack is associated with each sampling point. The location in the second stack is correspondingly determined accordingly by way of a vector with the same quantitative components, but the reverse sign as compared with the displacement vector for the first stack. The aim of the registration is to bring the image values at both locations into agreement. The square of the differences is therein regarded as the measure for an agreement. A further limit condition is that vectors directly adjoining the slice should have a similarity so that an overadaptation is prevented in order to ensure a "smoothness" of the displacement vector field.

Preferably, in an iterative method, in each step a minimizing vector is determined in each step on the basis of the current image values and image value gradients and a predetermined step length at the displaced sampling points and is added to the displacement vector which minimizes the square of the differences. In order to ensure a smoothness of the field, in each iteration step, a smoothing convolution or a low pass filtration is carried out on the vector field (e.g. a convolution with a Gaussian window). In the method used here, the step length and the width of the Gaussian window is adapted (lessened) in each iteration step. This is intended to have the effect that at the start large differences of the image values can be equalized by large displacements in large regions. With increasing step count, an adaptation to finer details can take place.

A further adaptation lies in a limitation of the resulting displacement vectors. Therein, via a suitable imaging function with "saturation behavior" it can be ensured that the displacement vector can exceed the stack boundaries only in a defined frame.

If the displacement vector nevertheless exceeds the stack boundaries, then the image values at the stack boundaries are preferably assumed to be continued perpendicularly to the boundary.

Regarding Step 5:

The displacement vectors are known at the regularly arranged sampling points of the boundary surfaces. If the displacement vector at another image point is needed as these sampling points, then it must be created from the known displacement vectors. Therein, it is firstly determined between which boundary slices the desired point lies. Here, it can occur that it does not lie between the boundary surfaces, but rather "before" or "after" the "first" or "last"

boundary surface. It is then assumed that a boundary surface on which all the displacement vectors are equal to zero lies at the start or the end of the final image volume. From the position, there then also results a clear association in which stack the image point lies. It is thus also known which vectors are to be taken into account on the boundary slices, since there for each image point, there are two different vectors, one which points "therebefore" and one which points "thereafter" in the stack.

The spacings of the image points from the boundary surfaces are then determined. From the ratio of the spacings, a weighted ratio is then produced with which the values of the two boundary slices are summed. The following apply herein: The closer slice receives the greater weighting. This is essentially equivalent to a linear interpolation between the two boundary slices, at least under the further conditions that the weighting has the sum 1 and the weighting has a linear relationship to the spacings. In general, another weighting can naturally also take place, also not necessarily with the sum 1.

Within the boundary slices, at the site of the image point projected onto the boundary slices an interpolation (bilinear) then also takes place. Therefrom, a trilinear interpolation of the displacement vectors between the two boundary slices takes place.

However, the interpolation can lead to an "unnatural" image impression. Severe distortions at the boundary slice then propagate very uniformly along the CT axis. A natural image impression is obtained by an additional smoothing process. This is obtained if before the interpolation, a convolution is carried out in the boundary slice with a Gaussian window. The spatial width of the window grows with the spacing of the image point from the boundary slice (e.g. linearly). This causes vividly a "relaxation" of the displacement vector field with increasing spacing from the boundary slice.

Regarding Step 6:

Two variants are preferred here as a specific embodiment.

In the image-based approach, according to the reconstruction in step 2), two image volumes are created. The reconstruction herein takes place according to the specifications of the CT user. The image points in both volumes are then present here in a regular spacing grid according to these specifications. In order to achieve the final image dataset, according to the displacement vectors obtained in step 5), the center point of each image point is displaced and then, with the known heart cycle an interpolation is performed at the site of the displaced center point of the two image volumes from the image data of the heart cycle associated with the image point. In the interpolation, a noise-retaining interpolation method is preferably used in order not to change the image impression (sharpness and noise behavior) locally.

In the reconstruction-based approach, the displacement vectors from step 5 are used directly in order to take account as early as during the reconstruction of the CT image data (e.g. by filtered back projection) of the displaced center points of the image points. In addition, the information regarding the selected heart cycle of an image point can also be taken into account by way of suitable weighting of the recording region. Finally, the image points are however then represented on a regular grid again. In this variant, the final image volume arises directly from the reconstruction with the properties according to the specifications of the CT user. This variant requires a somewhat more complex implementation of the reconstruction since the displaced image points must be taken into account. When the method is carried out, however, an approximate halving of the execution time results, as compared with the image-based approach, since only half of the image points must be generated.

Quite generally, a preferred method for actual practice can be described as follows:

a. preparing a CT recording so that from the CT recording data, partial image volumes (stacks) can be reconstructed, wherein each stack is characterized by a different weighting of the temporal proportions of the CT recording data.

b. estimating a spatial association with which the position of an image element in a stack can be associated with a position of this image element in another stack, if present.

c. generating weight and displacement vector quantities for each image point of a final 3D image point grid, wherein from each displacement vector a displaced center point of the image point results, wherein each displacement vector points to an image point in exactly one stack and wherein exactly one weight is associated with each vector and wherein each displaced center point points to a mapping of the same element in the different stacks.

d. reconstructing the final image volume in which, for each final image point, the image values and the displaced center points are determined and these image values are added weighted in order to obtain the final image value of the image point, which image points are represented in the regular grid of the final image volume.

The method set out in the method steps of the relatively specific method described above can be mapped as follows onto the steps of the more general method: 1. and 2. correspond to a., 3. and 4. correspond to b, 5. corresponds to c and 6. corresponds to d.

The relatively specific method is conceived, above all, for use with ECG-controlled recording for cardiac imaging. The relatively general can also be utilized for other applications, for example, for breathing-triggered CT recordings. Herein, for example, a breathing signal is available, on the basis of which the recording data can be "divided" into stacks. However, an ECG signal can be lacking so that here also discontinuities can occur, in particular in the region of the heart. In addition, via the breathing signal, the spatial arrangement of the organs in the thoracic cavity cannot be reproduced at any time with absolute reliability, so that even given the same breathing signal, different spatial arrangements can certainly be found and discontinuities are accordingly possible.

One extension provides, in particular, that apart from the actual image values, a data completeness can also be determined. It can thus be possible that there are image points in the edge region of the image volume of the stack which can still be reconstructed approximately, although for a correct reconstruction the CT rotation angle region available by way of the weighting is restricted and is therefore not complete. It is possible to complement these image points with a rotation angle portion of an adjacent slice that is available in the weighting window. The data completeness then permits these regions to be recognized and possibly to be avoided. However, due to edge effects, it can be favorable to enhance these image points in this way.

Regarding Step b:

In general, different registration methods are suitable here. Preferably, an image registration is undertaken in the whole overlap region or even therebeyond. Thus, a registration or spatial allocation is obtained not only for the boundary slice, but therebeyond. This can then be used, for example, in order to take account in one image point not only of the recording data of a stack, but of at least two. This increases the dose effect of the CT recording.

It is also preferred that a deep learning-based registration method is used which is trained to create the spatial arrangement.

Furthermore, it is preferred that during the determination of the boundary slice, initially all the displacement vectors are left at zero, but the position of the boundary slice along the CT axis is determined so that the squared differences are as small as possible from the outset. In order that the smallest possible displacement vectors can subsequently be reckoned with, which overall leads to a more natural image impression.

Even if a symmetry of the displacement vectors is preferred in the boundary slice, i.e. the displacement to the second stack is exactly inversely equivalent to the displacement to the first stack, it could be advantageous for the image impression to determine both vectors independently or at least more weakly coupled. However, the challenge with regard to stability is thereby greater since the number of free parameters increases.

If a data completeness is available, this can be taken into account in a registration method as a boundary condition. Regarding Step c:

By way of the generalization, it is possible that the recording data can contribute a plurality of stacks to a final image point. For this purpose, for example, from the spatial assignment of common image elements in the stacks, a central position of this image must be found, for example, in that the center of gravity is determined. Starting from the center of gravity, the displacement vectors relating to the image element can then be determined in all the stacks in which this image element can be found. These centers of gravity must then be transferred to a regular grid, so that for each grid point, the set of the vectors to the image elements can be generated.

Somewhat more specifically, a registration to a plurality of slices (that is a 3D grid rather than a 2D grid) is preferred in the overlap region. Thereby, in the overlap region, a denser set of displacement vectors is available, from which the displacement vector field can then be interpolated. Regarding Step d:

The reconstruction can again take place by way of interpolation at a displaced center point position in the image space or by including the displaced center points into the CT reconstruction (e.g. by back projection). It is preferred therein that more than one stack contributes to the final image value. For each stack which contributes, a similar procedure can be used and the final image value arises as a weighted sum of the individual stack amounts. For example, it is imaginable that at a very low pitch, in a spiral recording, more than two heart cycles can be covered at one position along the CT axis.

All the features of the practical method outlined here can also be used for the general method.

What is preferable is the use of AI-based (artificial intelligence) methods for the method according to one or more example embodiments of the present invention. An artificial intelligence system is based on the principle of machine-based learning and is typically carried out in a learning-capable algorithm that has been suitably trained. For machine-based learning, the expression "machine learning" is often used, wherein the principle of "deep learning" is also included therein. For example, a deep convolutional neural network (DCNN) is trained to restore a situation with a high dose (and thus with low noise) from CT images with a low dose (and thus with high noise). The situation with a high dose was therein known during training. What is problematic here, however, is an error estimation in the later application to unknown data since the training cannot in any case be complete and a generalization is, as a general rule, difficult to prove.

Preferably, components of one or more example embodiments of the present invention are present as a "cloud service". A cloud service of this type serves for processing data, in particular, via artificial intelligence, but can also be a service on the basis of conventional algorithms or a service in which an evaluation by humans takes place in the background. In general, a cloud service (identified in the following as a "cloud") is an IT infrastructure in which, for example, storage space or computing power and/or an application software is made available via a network. The communication between the user and the cloud takes place via data interfaces and/or data transfer protocols. In the present case, it is particularly preferred that the cloud service makes both computing power and also application software available.

In the context of a preferred method, a provision of data takes place via the network to the cloud service. This comprises a computer system, e.g. a computer cluster which typically does not comprise the local computer of the user. This cloud can be made available, in particular, by the medical facility which also provides the medical technology systems. For example, the data of an image recording is transmitted via an RIS (radiological information system) or a PACS to a (remote) computer system (the cloud). Preferably, the computer system of the cloud, the network and the medical technology system represent a group in the data technology sense. The method can therein be realized via a command combination in the network. The data ("results data") calculated in the cloud is transmitted again via the network to the local computer of the user.

BRIEF DESCRIPTION OF THE DRAWINGS

The present invention will now be described again in greater detail using exemplary embodiments, making reference to the accompanying drawings. In the various drawings, the same components are provided with identical reference signs. The drawings are in general not to scale. In the drawings.

DETAILED DESCRIPTION

In the following explanation, it is assumed that the imaging system is a computed tomography system. In principle, however, the method is also usable in other imaging systems.

Figure 1:
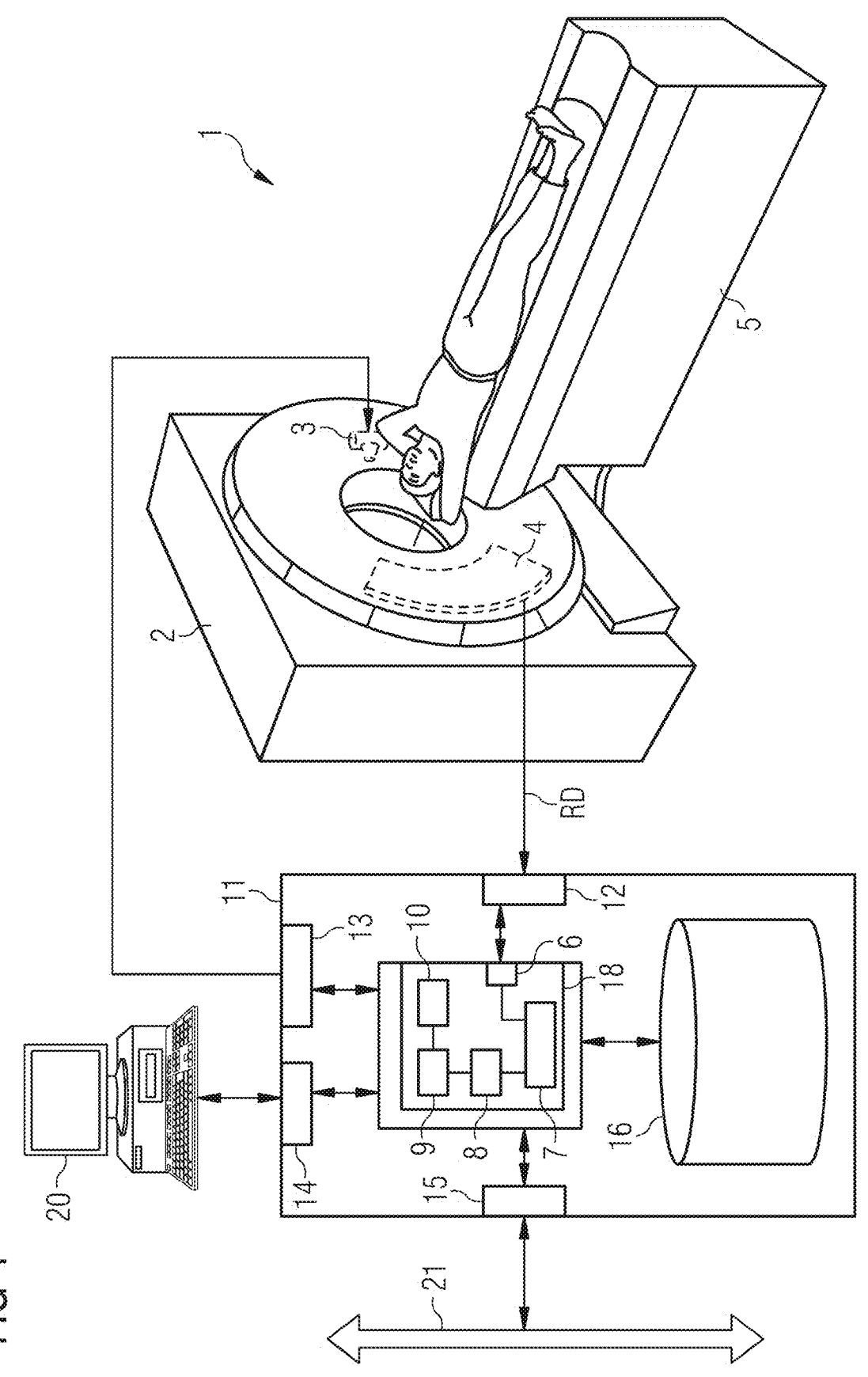
FIG. 1 is a coarse schematic representation of a computed tomography system with an exemplary embodiment of a control device with an apparatus according to the present invention for carrying out the method.

FIG. 1 shows, in a rough schematic form, a computed tomography system 1 having a control device 11 for carrying out the method according to an embodiment of the present invention. The computed tomography system 1 has, in the usual way, a scanner 2 with a gantry in which there rotates an X-ray source 3 which irradiates a patient, said patient being advanced via a support 5 into a scanning space of the gantry, so that the radiation impinges upon a detector 4 lying, in each case, opposite the X-ray source 3. It should be expressly noted that the exemplary embodiment according to this drawing is merely one example of a CT and the present invention can also be used with any desired CT designs, for example, with an annular, fixed X-ray detector and/or a plurality of X-ray sources.

Similarly, with the control device 11, only the components which are essential for the explanation of an embodiment of the present invention are shown. In principle, such CT systems and the associated control devices are known to persons skilled in the art and therefore do not need to be described in detail.

A core component of the control device 11 in this case is a processor on which the different components are realized in the form of software modules. The control device 11 also has a terminal interface 14 to which a terminal 20 is connected, via which an operator can operate the control device 11 and therefore the computed tomography system 1. A further interface 15 is a network interface for connecting to a data bus 21 in order thereby to create a connection to an RIS (radiology information service) or a PACS (picture archiving and communication system).

Via a control interface 13, the scanner 2 can be controlled by the control device 11, i.e. the rotational speed of the gantry, the displacement of the patient support 5 and the X-ray source 3 itself are controlled. Via an acquisition interface 12, the raw data RD is read out from the detector 4. Furthermore, the control device 11 comprises a storage unit 16 in which, inter alia, different scan protocols are stored.

As a software component, inter alia, a scan control unit is implemented on the processor. Via the control interface 13, this scan control unit controls the scanner 2, on the basis of one or more selected scan protocols which have possibly been modified by the user via the terminal 20, in order to carry out a scan and to acquire data.

A further component on the processor is an image data reconstruction unit 18, with which from the raw data RD acquired via the data acquisition interface 12, the desired image data is reconstructed. This image data reconstruction unit 18 is herein equipped as an apparatus 18 according to an embodiment of the present invention and comprises the following components. Reference should be made to the explanation of the method (see FIG. 3) for the function of the components.

A data interface 6 serves to receive CT recording data RD comprising recordings of a plurality of overlapping partial image volumes. Such a recording is sketched in FIG. 2.

Figure 2:
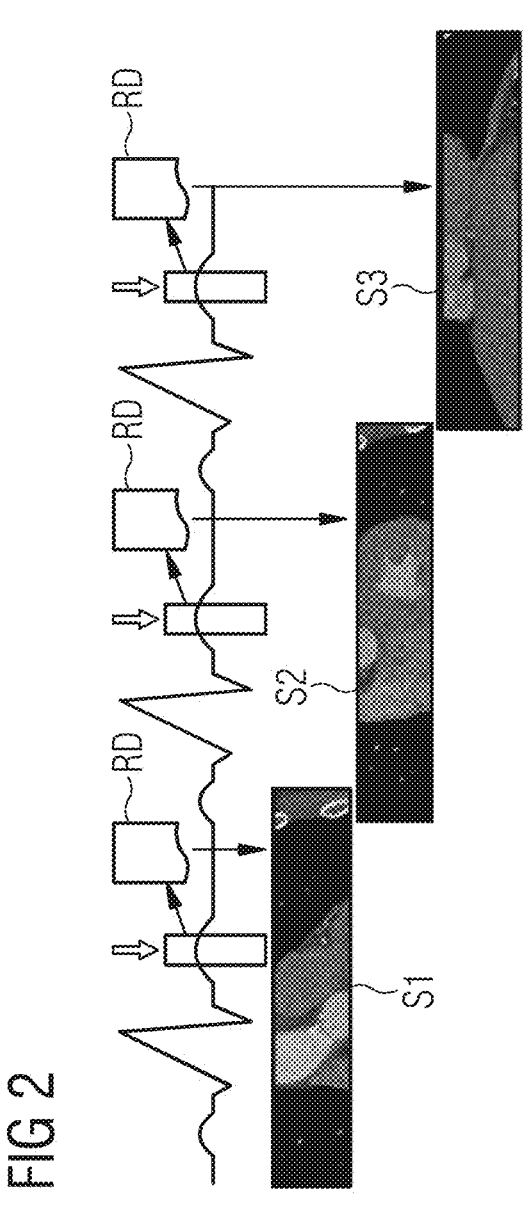
FIG. 2 is an ECG-controlled recording of partial images.

A working reconstruction unit 7 serves for reconstructing a working image dataset A from the CT recording data RD, wherein the working image dataset A comprises a plurality of partial images S1, S2, S3 (as shown in FIG. 2) wherein each partial image S1, S2, S3 has an overlap region U with at least one other partial image S1, S2, S3.

A displacement unit 8 serves for establishing displacement vectors V for registering the overlap regions of the partial images S1, S2, S3 (see e.g. FIG. 4), wherein a set of displacement vectors V is associated with each partial image S1, S2, S3 of the working image dataset A for two opposing side regions in each case, wherein in the event that a side region is not registered to another side region, a set of predetermined displacement vectors V is associated with this side region.

A vector field unit 9 serves for interpolating a displacement vector field VF for each partial image S1, S2, S3 from its sets of the displacement vectors V of the two side regions (see FIG. 5, for example), wherein two sides of the displacement vector field VF correspond to the respective sets of established displacement vectors V for this partial image S1, S2, S3 and the displacement vectors V are interpolated between the two sides on the basis of a predetermined transfer function from one set of displacement vectors V to the other set of displacement vectors V.

A second reconstruction unit 10 serves for creating an output image dataset AD on the basis of the CT recording data RD and the displacement vector fields VF. Theoretically, the working reconstruction unit 7 can also be used for this if it is configured accordingly.

The data interface 6 can also serve herein for outputting the output image dataset AD. However, the terminal interface 14 can also be used.

FIG. 2 shows an ECG-controlled recording of partial images S1, S2, S3. What is shown is an ECG heart trace in which recording time points are indicated with rectangular boxes and arrows. During the recordings, raw data RD is recorded which (can be) reconstructed as shown to partial images S1, S2, S3.

Figure 3:
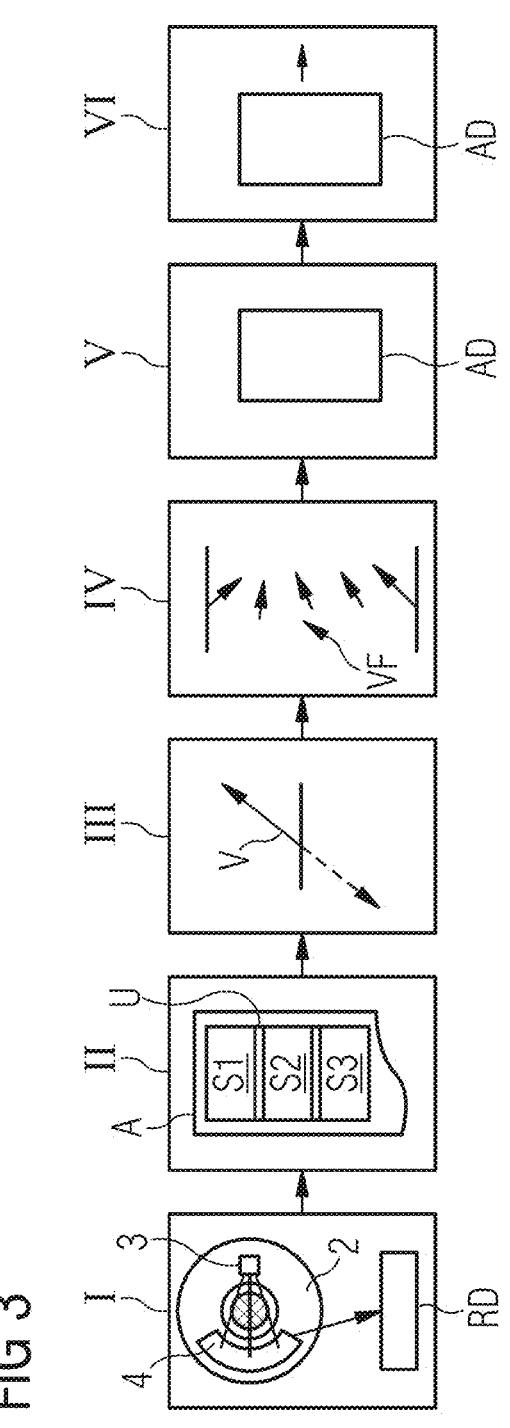
FIG. 3 is a schematic representation of the inventive method.

FIG. 3 shows a schematic representation of the method according to an embodiment of the present invention for reconstructing CT images.

In step I, a provision of CT recording data RD comprising recordings of a plurality of overlapping partial image volumes takes place, as shown, for example, in FIG. 2.

In step II, a reconstruction of a working image dataset A from the CT recording data RD takes place, wherein the working image dataset A comprises a plurality of partial images S1, S2, S3, wherein each partial image S1, S2, S3 has at least one overlap region U with at least one further partial image S1, S2, S3.

In step III, displacement vectors V for registering the overlap regions of the partial images S1, S2, S3 to one another are established (see e.g. FIG. 4), wherein a set of displacement vectors V is associated with each partial image S1, S2, S3 of the working image dataset A for two opposing side regions in each case, wherein in the event that a side region is not registered to another side region, a set of predetermined displacement vectors V is associated with this side region.

In step IV, a displacement vector field VF for each partial image S1, S2, S3 is interpolated from its sets of the displacement vectors V of the two side regions (see e.g. FIG. 5), wherein two sides of the displacement vector field VF correspond to the respective sets of established displacement vectors V for this partial image S1, S2, S3 and the displacement vectors V are interpolated between the two sides on the basis of a predetermined transfer function from one set of displacement vectors V to the other set of displacement vectors V.

In step V, an output image dataset AD is created on the basis of the CT recording data RD and the displacement vector fields VF.

In step VI, the output of the output image dataset AD takes place.

Figures 4, 5:
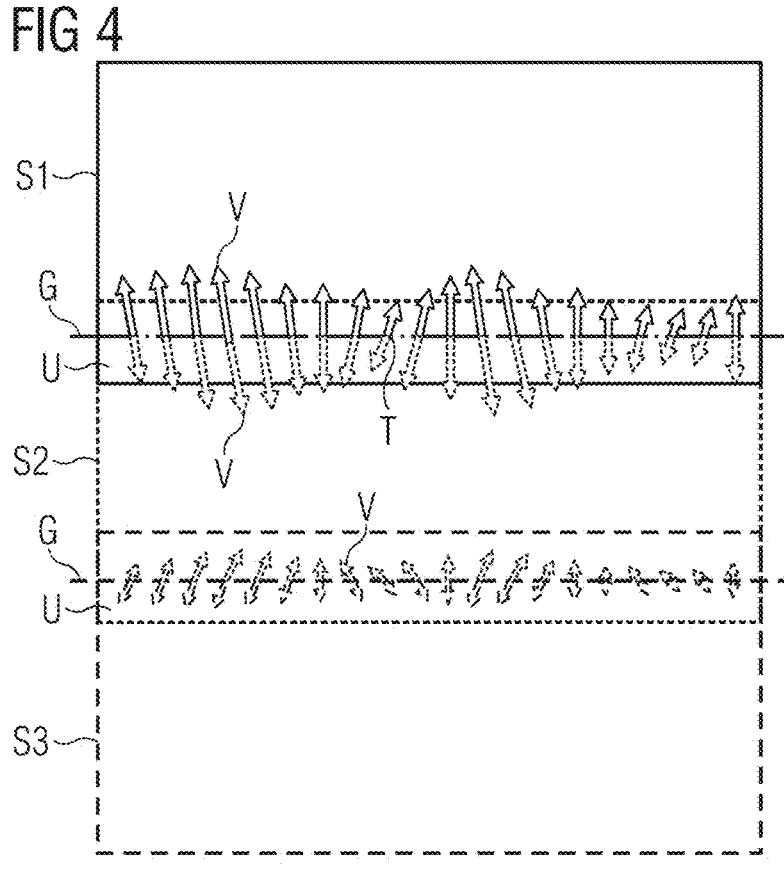
FIG. 4 is three partial images with boundary slices and displacement vectors.
FIG. 5 is the interpolation of a displacement vector field.

FIG. 4 shows three partial images S1, S2, S3 with boundary slices G and displacement vectors V in the overlap region U of the respective partial images S1, S2, S3. The side regions are therein located above and below and are not shown, since it is not only parts of the partial images S1, S2, S3 that are involved. For example, the upper edge and the overlap region U with the second partial image or possibly the boundary slice G in this overlap region U can be regarded as side regions of the upper partial image S1. In general, the expression "side region" should only unite the cases that two overlap regions U are present or an overlap region and an edge region (without an overlap).

The displacement vectors V originate paired, in each case, from sampling points T in the planar boundary slice and here are directed away from the boundary slice G (they are inverse to one another). They point in pairs to image regions in the partial images S1, S2, S3 associated with them, wherein the upper vectors point into the respective upper partial image S1, S2 and the lower vectors point into the respective lower partial image S2, S3. The image regions to which they point are those image regions in the partial images S1, S2, S3 the image value of which is to be associated with the respective sampling point T which forms the foot point of the vector pair. These relevant image regions should thus show identical regions of the recorded motif.

It is a certain challenge to achieve a result with the given conditions (inverse vector pairs, planar boundary slice G in the center of the overlap region U). The only degrees of freedom are then represented by the vector coordinates, which however is bound to the condition of pointing to the same regions of the motif. However, this can be achieved with corresponding minimizing methods.

FIG. 5 shows the interpolation of a displacement vector field VF from sets of the displacement vectors V of both side regions of the central partial image S2 of FIG. 4. Shown above and below are the boundary slices G, from which the two sets of the displacement vectors V emerge. Therebetween, further displacement vectors V are interpolated between the two side regions so that these displacement vectors V represent a soft transition from the one set of displacement vectors V to the other set of displacement vectors V.

Figure 6:
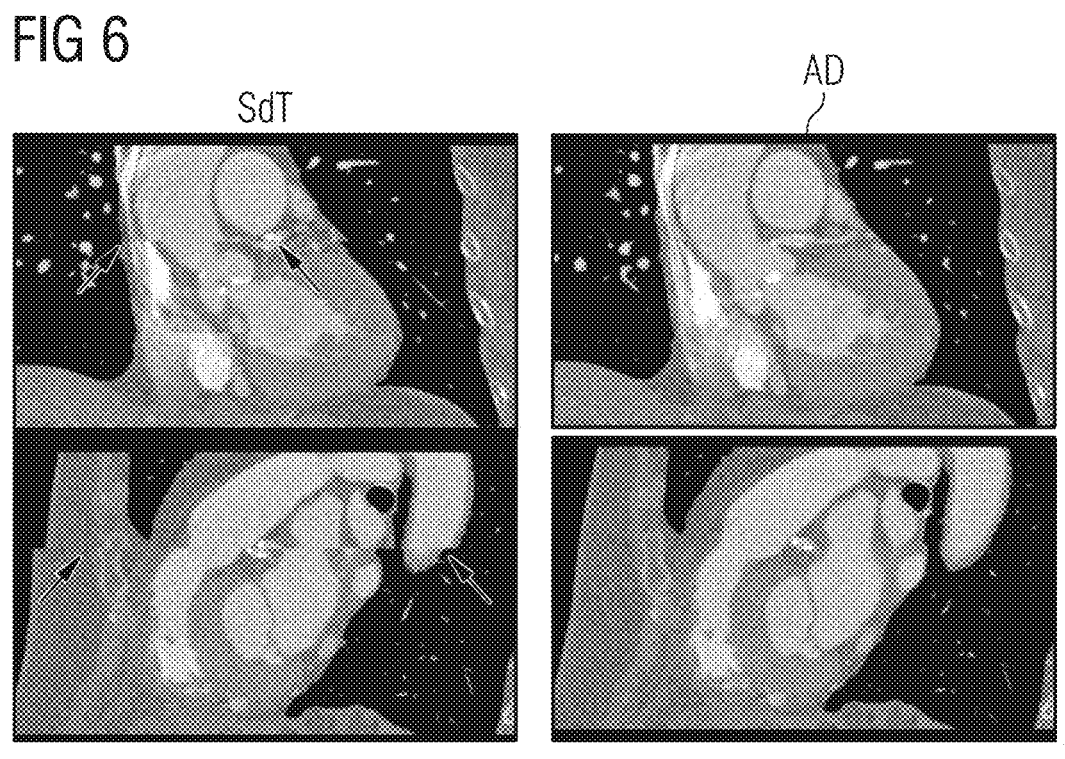
FIG. 6 is a comparison of an output image dataset with an image dataset according to the prior art.
Figure 7:
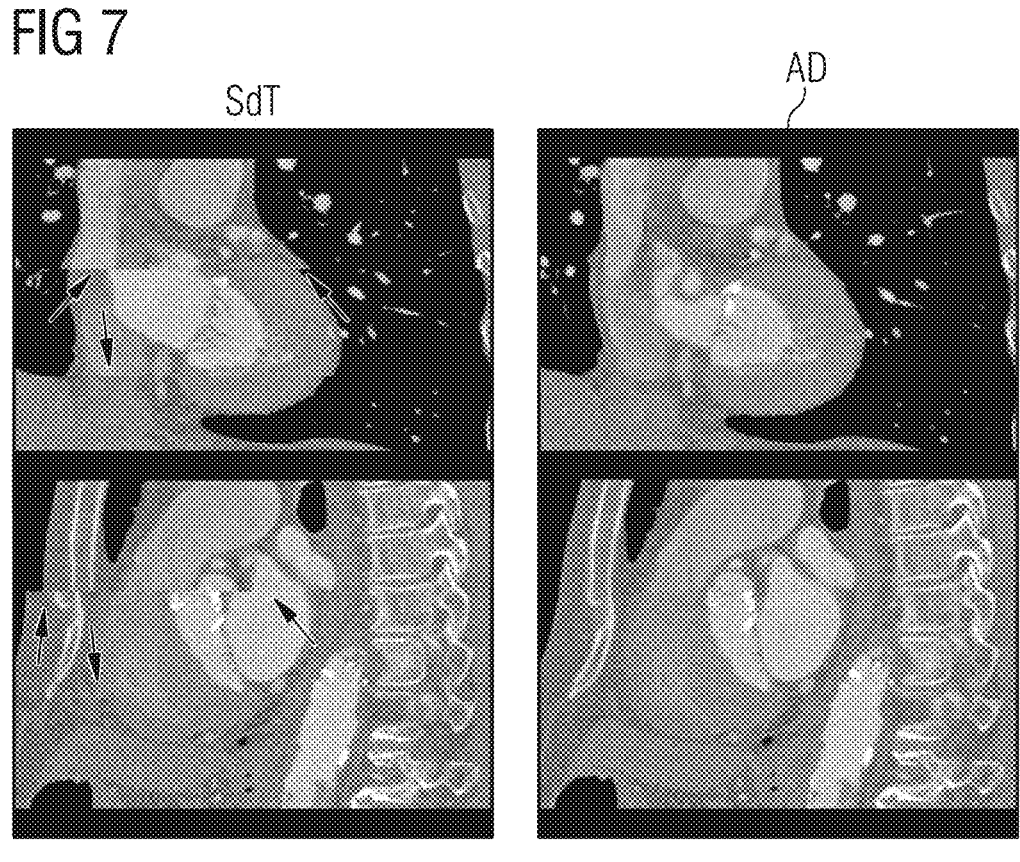
FIG. 7 is a comparison of an output image dataset with an image dataset according to the prior art.

FIGS. 6 and 7 show a comparison of an output image dataset AD (right) with an image dataset according to the prior art (left) after a "true stack" reconstruction. In the images on the left-hand side, a horizontal line is visible along the arrows on which there is a clear offset between the upper image part and the lower image part in each case. This offset is no longer visible in the right-hand images.

Finally, it should again be noted that the methods described above in detail and the computed tomography system 1 disclosed are merely exemplary embodiments which can be modified by a person skilled in the art in a wide variety of ways without departing from the scope of the present invention.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single micropro- cessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combina- tion of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer- readable medium is therefore considered tangible and non- transitory. Non-limiting examples of the non-transitory com- puter-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (includ- ing, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Furthermore, as mentioned similarly above the use of the indefinite article "a" or "an" does not preclude the possibil- ity that the relevant features can also be present plurally. Similarly, the expressions "unit" and "module" do not preclude the components in question from consisting of a plurality of cooperating partial components with can also be spatially distributed. The expression "a number" is to be understood as meaning "at least one".

What is claimed is:

1. A method for reconstructing Computed Tomography (CT) images, the method comprising:
    providing CT recording data including recordings of a plurality of overlapping partial image volumes;
    reconstructing a working image dataset from the CT recording data, the working image dataset including a plurality of partial images, and each respective partial image among the plurality of partial images having an overlap region with at least one corresponding partial image from among the plurality of partial images such that the plurality of partial images includes a plurality of overlap regions;
    establishing subsets of displacement vectors associated with two opposing side regions of each of the plurality of partial images;
    interpolating a corresponding displacement vector field for each respective partial image among the plurality of partial images from the subsets of the displacement vectors associated with the two opposing side regions of the respective partial image to obtain a plurality of displacement vector fields, two sides of the correspond- ing displacement vector field corresponding to the subsets of the displacement vectors, the interpolating including interpolating the subsets of the displacement vectors between the two sides of the corresponding displacement vector field based on a transfer function from a first subset of the displacement vectors to a second subset of the displacement vectors, and the subsets of the displacement vectors including the first subset and the second subset;
    creating an output image dataset based on the CT record- ing data and the plurality of displacement vector fields; and
    outputting the output image dataset.

2. The method as claimed in claim 1, wherein the estab- lishing comprises:
    establishing a third subset of the displacement vectors for registering a first overlap region between a first partial image and a second partial image, the establishing the third subset of the displacement vectors including determining a two-dimensional boundary slice in the first overlap region, the first overlap region being among the plurality of overlap regions, and the plural- ity of partial images including the first partial image and the second partial image.

3. The method as claimed in claim 2, wherein the two- dimensional boundary slice is a plane perpendicular to a CT axis.

4. The method as claimed in claim 3, wherein the two- dimensional boundary slice is at a central position within boundaries of the first overlap region.

5. The method as claimed in claim 2, wherein the deter- mining of the two-dimensional boundary slice comprises:
    assuming a set of displacement vectors with a value; and

determining a position of the two-dimensional boundary slice along a CT axis such that quadratic differences of image values are at a minimum.

6. The method as claimed in claim 1, further comprising:
defining a regular 2D grid of sampling points in a first overlap region of a first partial image among the plurality of partial images, the first overlap region being among the plurality of overlap regions; and
associating a respective displacement vector with each sampling point among the regular 2D grid of the sampling points to obtain a third subset of the displacement vectors.

7. The method as claimed in claim 6, wherein
the respective displacement vector points to a location in the first partial image from a corresponding sampling point among the sampling points; and
the regular 2D grid of the sampling points are at least one of equidistant or form a boundary slice.

8. The method as claimed in claim 7, wherein a side region of the first partial image is defined based on the sampling points and a set of displacement vectors is associated with the side region of the first partial image, the set of displacement vectors including the third subset of the displacement vectors.

9. The method as claimed in claim 1, wherein the displacement vectors include a first displacement vector associated with a first sampling point of a first partial image and a second displacement vector associated with a corresponding sampling point of a second partial image, the first sampling point and the corresponding sampling point being in a first overlap region of the first partial image and the second partial image, the plurality of partial images including the first partial image and the second partial image, and the plurality of overlap regions including the first overlap region.

10. The method as claimed in claim 9, wherein the second displacement vector represents an inverse vector of the first displacement vector.

11. The method as claimed in claim 9, further comprising:
determining the first displacement vector and the second displacement vector based on a first measure used for a similarity of image regions of the first partial image and the second partial image, the first measure being based on a square of differences of image values; and
determining, via an iterative method, a minimizing vector based on current image values and image value gradients of the first partial image and the second partial image, the determining the minimizing vector being performed stepwise based on a step length at respectively displaced sampling points, and the minimizing vector being based on the first measure.

12. The method as claimed in claim 1, wherein the establishing includes setting values of a third subset of the displacement vectors for first image regions of the plurality of partial images to a first value, the first image regions having an image value below a limit value, and the limit value being above an air CT value.

13. The method as claimed in claim 12, wherein the limit value is between −1000 HU and −800 HU.

14. The method as claimed in claim 1, wherein the interpolating comprises:
determining spacings of a relevant image region from two opposing side regions of a first partial image among the plurality of partial images, the relevant image region being between the two opposing side regions of the first partial image;

determining a weighted relationship of the spacings from the two opposing side regions of the first partial image, a closer side region among the two opposing side regions of the first partial image having a greater weight in the weighted relationship;
calculating a first displacement vector based on a ratio and a vector addition of a second displacement vector in a first side region and a third displacement vector in a second side region, the second displacement vector being among the first subset of the displacement vectors, the third displacement vector being among the second subset of the displacement vectors, and the first side region and the second side region being among the two opposing side regions of the first partial image;
determining a minimizing vector based on current image values and image value gradients of two partial images among the plurality of partial images, the two partial images including the first partial image, the two partial images having a first overlap region in the first side region or the second side region, the minimizing vector being based on a first measure, the determining the minimizing vector being performed stepwise based on a step length at respectively displaced sampling points, and the first overlap region being among the plurality of overlap regions; and
adding the minimizing vector to the first displacement vector.

15. The method as claimed in claim 1, further comprising:
performing a smoothing of a third subset of the displacement vectors in a first overlap region or a first displacement vector field between two opposing side regions of a first partial image among the plurality of partial images, the first overlap region being among the plurality of overlap regions, the first displacement vector field being among the plurality of displacement vector fields; and
at least one of
performing a smoothing convolution or a low pass filtration to establish the third subset of the displacement vectors in the first overlap region, or
performing a convolution with a Gaussian window in the first overlap region before interpolating the first displacement vector field.

16. The method as claimed in claim 15, wherein
the first overlap region is a boundary slice; or
the third subset of the displacement vectors in the first overlap region are established using a convolution with a Gaussian window.

17. The method as claimed in claim 1, wherein
the creating the output image dataset includes
reconstructing the plurality of partial images,
displacing image regions of the plurality of partial images according to the plurality of displacement vector fields, and
assembling the plurality of partial images based on the displacing; or
the creating the output image dataset includes reconstructing the plurality of partial images based on the plurality of displacement vector fields using a back projection, a region of the output image dataset being formed based on information from first partial images among the plurality of partial images by weighting corresponding contributions of the first partial images.

18. The method as claimed in claim 17, wherein the output image dataset has a greater image resolution than the working image dataset.

19. The method as claimed in claim 1, wherein at least one of the output image dataset or the plurality of partial images are reconstructed via a different weighting of temporal portions of the CT recording data, the weighting being based on weighting values determined for a plurality of image points of the output image dataset or the plurality of partial images.

20. The method as claimed in claim 19, wherein the plurality of image points form a 3D image data grid; and a weight is associated with a number of displacement vectors.

21. The method as claimed in claim 1, further comprising:

reconstructing the output image dataset by performing a first operation based on first image points in a first partial image lack data for reconstruction, the first image points being in an overlap region of the first partial image and a second partial image, the first partial image and the second partial image being included among the plurality of partial images, and the first operation including enhancing data of the first image points based on a displacement vector field of the second partial image, the displacement vector field of the second partial image being among the plurality of displacement vector fields, or using second image points of the second partial image without using the first image points.

22. The method as claimed in claim 1, wherein the plurality of partial images are stacks.

23. An apparatus for reconstructing Computed Tomography (CT) images, the apparatus comprising:

a first data interface configured to receive CT recording data including recordings of a plurality of overlapping partial image volumes;

a working reconstruction unit configured to reconstruct a working image dataset from the CT recording data, the working image dataset including a plurality of partial images, and each respective partial image among the plurality of partial images having an overlap region with at least one corresponding partial image from among the plurality of partial images such that the plurality of partial images includes a plurality of overlap regions;

a displacement unit configured to establish subsets of displacement vectors associated with two opposing side regions of each of the plurality of partial images;

a vector field unit configured to interpolate a corresponding displacement vector field for each respective partial image among the plurality of partial images from the subsets of the displacement vectors associated with the two opposing side regions of the respective partial image to obtain a plurality of displacement vector fields, two sides of the corresponding displacement vector field corresponding to the subsets of the displacement vectors, the interpolation including interpolating the subsets of the displacement vectors between the two sides of the corresponding displacement vector field based on a transfer function from a first subset of the displacement vectors to a second subset of the displacement vectors, and the subsets of the displacement vectors including the first subset and the second subset;

a second reconstruction unit configured to create an output image dataset based on the CT recording data and the plurality of displacement vector fields; and a second data interface configured to output the output image dataset.

24. A control device configured to control a computed tomography system, the control device including the apparatus as claimed in claim 23.

25. A computed tomography system comprising a control device as claimed in claim 24.

26. A non-transitory computer program product comprising a program that, when executed by a computer, causes said computer to carry out the method as claimed in claim 1.

27. A non-transitory computer-readable storage medium comprising computer-readable instructions that, when executed by a computer, cause said computer to carry out the method as claimed in claim 1.

28. An apparatus for reconstructing CT images, the apparatus comprising:

at least one processor configured to execute computer-executable instructions to cause the apparatus to receive CT recording data including recordings of a plurality of overlapping partial image volumes, reconstruct a working image dataset from the CT recording data, the working image dataset including a plurality of partial images, and each respective partial image among the plurality of partial images having an overlap region with at least one corresponding partial image from among the plurality of partial images such that the plurality of partial images includes a plurality of overlap regions, establish subsets of displacement vectors associated with two opposing side regions of each of the plurality of partial images, interpolate a corresponding displacement vector field for each respective partial image among the plurality of partial images from the subsets of the displacement vectors associated with the two opposing side regions of the respective partial image to obtain a plurality of displacement vector fields, two sides of the corresponding displacement vector field corresponding the subsets of the displacement vectors, the interpolation including interpolating the subsets of the displacement vectors between the two sides of the corresponding displacement vector field based on a transfer function from a first subset of the displacement vectors to a second subset of the displacement vectors, and the subsets of the displacement vectors including the first subset and the second subset, create an output image dataset based on the CT recording data and the plurality of displacement vector fields, and output the output image dataset.

* * * * *